US012576101B2

(12) United States Patent
Tsai et al.

(10) Patent No.: US 12,576,101 B2
(45) Date of Patent: Mar. 17, 2026

(54) APPLICATION BASED NUCLEOTIDES OF LACTOBACILLUS RHAMNOSUS TO PREPARE A COMPOSITION FOR ANTI-LIPOGENESIS

(71) Applicant: GenMont Biotech Incorporation, Tainan City (TW)

(72) Inventors: Wan-Hua Tsai, Kaohsiung City (TW); Yi-Ting Fang, Tainan City (TW); Chia-Yu Chang, Tainan City (TW); Hsueh-Te Lee, Kaohsiung City (TW)

(73) Assignee: GenMont Biotech Incorporation, Tainan City (TW)

( * ) Notice: Subject to any disclaimer, the term of this patent is extended or adjusted under 35 U.S.C. 154(b) by 0 days.

(21) Appl. No.: 18/677,546

(22) Filed: May 29, 2024

(65) Prior Publication Data

US 2025/0249028 A1     Aug. 7, 2025

(30) Foreign Application Priority Data

Feb. 6, 2024    (TW) .................................. 113104601

(51) Int. Cl.
| | |
|---|---|
| *A61K 31/713* | (2006.01) |
| *A61K 35/747* | (2015.01) |
| *A61P 3/06* | (2006.01) |
| *C12N 1/20* | (2006.01) |
| *C12N 15/113* | (2010.01) |
| *C12R 1/225* | (2006.01) |

(52) U.S. Cl.
CPC .......... *A61K 31/713* (2013.01); *A61K 35/747* (2013.01); *A61P 3/06* (2018.01); *C12N 1/20* (2013.01); *C12N 15/113* (2013.01); *C12R 2001/225* (2021.05)

(58) Field of Classification Search
CPC .. A61K 31/713; A61K 35/747; C12N 15/113; C12N 2001/225; A61P 3/06
USPC ..................... 435/6.1, 91.1, 91.31, 455, 458; 514/44 A; 536/23.1, 24.5
See application file for complete search history.

(56) References Cited

FOREIGN PATENT DOCUMENTS

TW          202229540 A       8/2022

OTHER PUBLICATIONS

Thomalla M., et al., "Evidence of an antiinflammatory toll-like receptor 9 (TLR 9) pathway in adipocytes," Journal of Endocrinology, vol. 240(2), 2019, p. 325-343.
Nihashi Y., et al., "Identification of a Novel Osteogenetic Oligodeoxynucleotide (osteoDN) That Promotes Osteoblast Differentiation in a TLR9-Independent Manner," Nanomaterials, vol. 12(10), 2022, 1680, https://doi.org/10.3390/nano12101680.

*Primary Examiner* — Jane J Zara
(74) *Attorney, Agent, or Firm* — MUNCY, GEISSLER, OLDS & LOWE, P.C.

(57) ABSTRACT

An application based on nucleotide fragments of *Lactobacillus rhamnosus* GM-020, to prepare a composition for anti-lipogenesis. The *Lactobacillus rhamnosus* GM-020 was deposited on Dec. 18, 2003 and has the CCTCC designation number CCTCC M203098. Also provided is a composition containing *Lactobacillus rhamnosus* GM-020 or nucleotide fragments thereof as effective ingredients for anti-lipogenesis.

3 Claims, 9 Drawing Sheets
Specification includes a Sequence Listing.

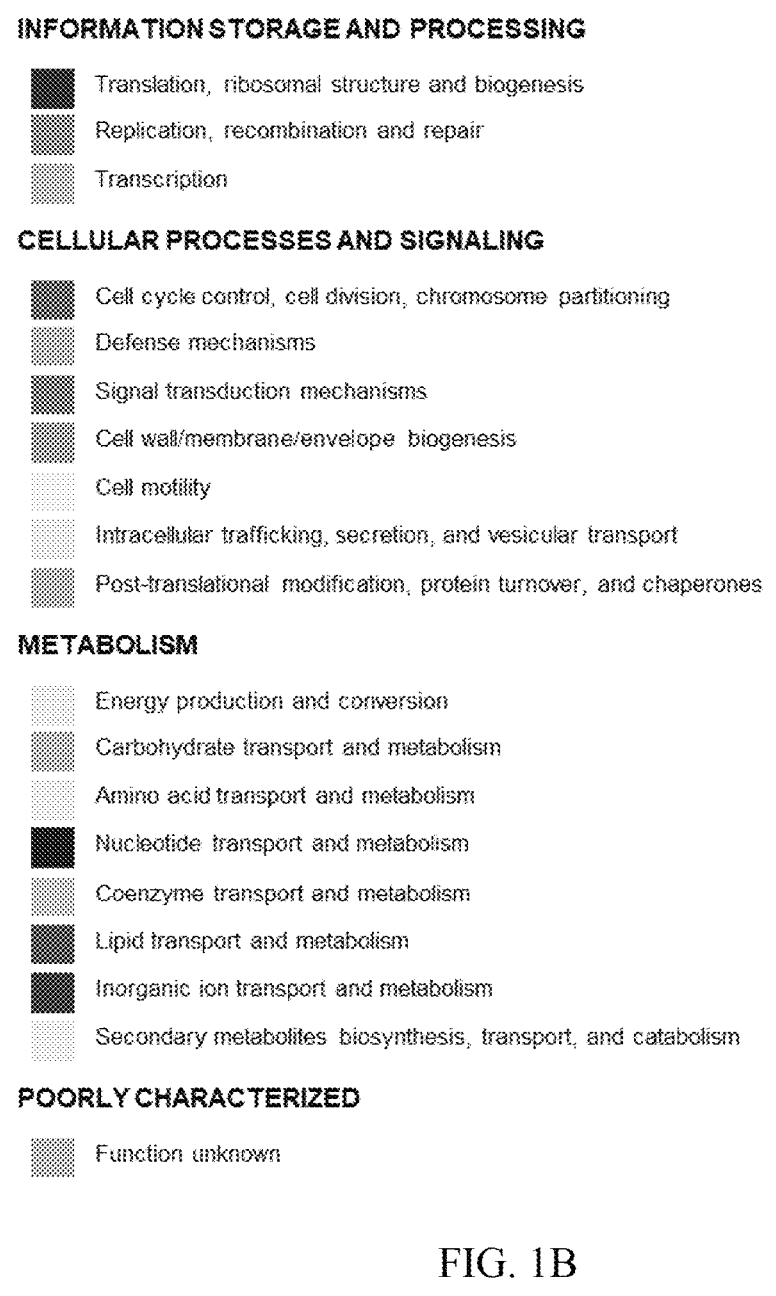

INFORMATION STORAGE AND PROCESSING

Translation, ribosomal structure and biogenesis

Replication, recombination and repair

Transcription

CELLULAR PROCESSES AND SIGNALING

Cell cycle control, cell division, chromosome partitioning

Defense mechanisms

Signal transduction mechanisms

Cell wall/membrane/envelope biogenesis

Cell motility

Intracellular trafficking, secretion, and vesicular transport

Post-translational modification, protein turnover, and chaperones

METABOLISM

Energy production and conversion

Carbohydrate transport and metabolism

Amino acid transport and metabolism

Nucleotide transport and metabolism

Coenzyme transport and metabolism

Lipid transport and metabolism

Inorganic ion transport and metabolism

Secondary metabolites biosynthesis, transport, and catabolism

POORLY CHARACTERIZED

Function unknown

FIG. 1B

|  | GM-020 |
| --- | --- |
| Species | rhamnosus |
| Size (bp) | 3,037,161 |
| G+C content (%) | 46.82 |
| Total genes | 2,895 |
| Coding content (%) | 86.09 |
| Gene average length (bp) | 783 |
| Genes assigned to COGs | 2,353 (81.3%) |
| Chromosome | 1 |
| rRNA operons | 5 |
| tRNA | 61 |
| plasmids | 0 |
| Transposases | 13 |
| CRISPR loci | 1 |
| Prophage-like clusters | 1 |
| Bacteriocin | 1 |

FIG. 1C

SEQUENCE LISTING

```
Sequence total quantity: 9
SEQ ID NO: 1              moltype = DNA   length = 20
FEATURE                   Location/Qualifiers
source                    1..20
                          mol_type = genomic DNA
                          organism = Lactobacillus rhamnosus
                          strain = GM-020
SEQUENCE: 1
ccattttcaa gcttgacttt                                                    20

SEQ ID NO: 2              moltype = DNA   length = 20
FEATURE                   Location/Qualifiers
source                    1..20
                          mol_type = genomic DNA
                          organism = Lactobacillus rhamnosus
                          strain = GM-020
SEQUENCE: 2
gacatttcaa gcttgaacaa                                                    20

SEQ ID NO: 3              moltype = DNA   length = 20
FEATURE                   Location/Qualifiers
source                    1..20
                          mol_type = genomic DNA
                          organism = Lactobacillus rhamnosus
                          strain = GM-020
SEQUENCE: 3
ttggtgtcaa gcttgacatc                                                    20

SEQ ID NO: 4              moltype = DNA   length = 20
FEATURE                   Location/Qualifiers
source                    1..20
                          mol_type = genomic DNA
                          organism = Lactobacillus rhamnosus
                          strain = GM-020
SEQUENCE: 4
tcaggctcaa gcttgagttc                                                    20

SEQ ID NO: 5              moltype = DNA   length = 20
FEATURE                   Location/Qualifiers
source                    1..20
                          mol_type = genomic DNA
                          organism = Lactobacillus rhamnosus
                          strain = GM-020
SEQUENCE: 5
taggactcaa gcttgatctc                                                    20

SEQ ID NO: 6              moltype = DNA   length = 21
FEATURE                   Location/Qualifiers
source                    1..21
                          mol_type = other DNA
                          note = FAS gene Forward primer
                          organism = Synthetic construct
SEQUENCE: 6
ggaggtggtg atagccggta t                                                  21

SEQ ID NO: 7              moltype = DNA   length = 21
FEATURE                   Location/Qualifiers
source                    1..21
                          mol_type = other DNA
                          note = FAS gene Reverse primer
                          organism = Synthetic construct
SEQUENCE: 7
tgggtaatcc atagagccca g                                                  21

SEQ ID NO: 8              moltype = DNA   length = 20
FEATURE                   Location/Qualifiers
source                    1..20
                          mol_type = other DNA
                          note = GAPDH gene Forward primer
                          organism = Synthetic construct
SEQUENCE: 8
tgcaccacca actgcttagc                                                    20
```

-continued

```
SEQ ID NO: 9           moltype = DNA   length = 21
FEATURE                Location/Qualifiers
source                 1..21
                       mol_type = other DNA
                       note = GAPDH gene Reverse primer
                       organism = synthetic construct
SEQUENCE: 9
ggcatggact gtggtcatga g                                                21
```

APPLICATION BASED NUCLEOTIDES OF *LACTOBACILLUS RHAMNOSUS* TO PREPARE A COMPOSITION FOR ANTI-LIPOGENESIS

CROSS-REFERENCE TO RELATED APPLICATIONS

The present application claims priority of Application No. 113104601, filed in Taiwan, R.O.C. on Feb. 6, 2024 under 35 U.S.C. § 119, the entire contents of all of which are hereby incorporated by reference.

REFERENCE TO AN ELECTRONIC SEQUENCE LISTING

The content of the electronic sequence listing (PB20230480_sequence.xml; Size: 12,986 bytes; and Date of Creation: Jan. 21, 2026) is herein incorporated by reference in its entirety.

BACKGROUND OF THE INVENTION

Brief Discussion of the Related Art

The effect of *L. rhamnosus* on regulation of adipogenesis had been verified in recent research. For example, the benefits of calcium ions for anti-obesity, inhibiting generation of the adipose tissue and more lipid oxidation in muscles, can be consolidated with fermented milk containing *L. rhamnosus* GG ingested. Moreover, *L. rhamnosus* 86 proves effective in inhibiting differentiation of adipocytes as well as lipogenesis and correcting obesity attributed to fat-rich diets. However, the functions of *L. rhamnosus* engaging in fat reduction and regulating the anti-obesity mechanism still need to be clarified by more evidence. Excessive lipid accumulation is attributed to two dysfunctional mechanisms: (1) excessive lipogenesis; (2) fatty acid oxidation or lipodieresis impaired. Reportedly, genes such as FAS (Fatty acid synthase), ACC (acetyl coenzymeA carboxylase), SREBP1 (sterol regulatory element-binding transcription factor) and SCD1 (stearoyl coenzymeA desaturase 1), all of which are classified as lipogenesis-related genes, feature over-expression of genes/proteins promoting lipogenesis.

In the whole genome sequence of a bacterium, some oligodeoxynucleotide (ODN) fragments are characteristic of the physiological effect for immunoregulation. For example, the copy number of TTAGGG (SEQ ID NO. 10) and TCAAGCTTGA (SEQ ID NO. 12) in *Lactobacillus paracasei* is higher than the number of pathogenic bacteria or Escherichia coli and ODN synthesized based on the sequences contributes to inhibiting activation of dendritic cells in the intestinal lamina propria (Bouladoux et al.). Moreover, the sequence of TTTCGTTT (SEQ ID NO. 11) presented in *L. rhamnosus* GG has effects on immune stimulation, such as B cells proliferation and Th1 activation. As shown in arthritis of mice, the sequence of CCTCAAGCTTGAGGGG (SEQ ID NO. 13) features anti-inflammation and corrects serious arthritis significantly. However, there is no report of CpG-ODNs in probiotics engaging in regulation of lipogenesis.

Accordingly, how to find oligodeoxynucleotide fragments in probiotics with the function of regulating lipogenesis is the issue explored in the present disclosure.

FIELD OF THE INVENTION

The present disclosure relates to nucleotides of *Lactobacillus rhamnosus*, as known as *Lacticaseibacillus rhamno-sus*, for anti-lipogenesis, this is effectuated by inhibiting generation of lipid droplets in adipocytes particularly.

BRIEF SUMMARY OF THE INVENTION

After years of research and considering the issues mentioned above, the patent inventor has separated oligodeoxy nucleotide (ODN) fragments of probiotics, *Lactobacillus rhamnosus*, for anti-lipogenesis effectively as a novel and safe preventive measure for obesity attributed to fat-rich diets.

To this end, the present invention discloses a nucleotide which is effective in anti-lipogenesis and given SEQ ID NO: 1 as the sequence number.

The present invention also discloses a nucleotide which is effective in anti-lipogenesis and given SEQ ID NO: 5 as the sequence number.

The present invention further discloses a composition contributing to anti-lipogenesis and containing *Lactobacillus rhamnosus* GM-020, or nucleotide fragments thereof, as effective ingredients. *Lactobacillus rhamnosus* GM-020 was deposited on Dec. 18, 2003 and has the CCTCC designation number CCTCC M203098, and the nucleotide fragments contain the sequence of SEQ ID NO. 1 or SEQ ID NO. 5.

In one embodiment of the present disclosure, the composition is taken as a pharmaceutical composition, a nutritional supplement, or healthcare food.

In one embodiment of the present disclosure, the composition further comprises pharmaceutically acceptable vehicles.

In one embodiment of the present disclosure, the composition is a solution, a suspension liquid, an emulsion, powders, a pastille, a pill, syrup, an oral ingot, a tablet, a chewing gum, a thick juice, or a capsule.

In one embodiment of the present disclosure, the composition further comprises an editable material selected from water, a fluid dairy product, milk, condensed milk, a yogurt, a frozen yogurt, a lactic acid fermented beverage, milk powders, an ice cream, a cream, a cheese, soy milk, fermented soy milk, a vegetable juice, a fruit juice, a sports drink, a dessert, a jelly, a confection, baby food, healthcare food, an animal fodder, a Chinese herbal medicine, or a dietary supplement.

The present invention further discloses an application based on nucleotide fragments of *Lactobacillus rhamnosus* GM-020, to prepare a composition featuring anti-lipogenesis and containing *Lactobacillus rhamnosus* GM-020, or nucleotide fragments thereof as effective ingredients. *Lactobacillus rhamnosus* GM-020 was deposited on Dec. 18, 2003 and has the CCTCC designation number CCTCC M203098, and the nucleotide fragments contain the sequence of SEQ ID NO. 1 or SEQ ID NO. 5. In one embodiment of the present disclosure, the anti-lipogenesis means inhibition of lipid droplets generated in adipocytes.

In one embodiment of the present disclosure, the anti-lipogenesis is effectuated by reducing expression of the lipogenesis-related gene, FAS, inside adipocytes.

In the present disclosure, the effects of some specific oligodeoxynucleotide fragments, that is, IM1: TTAGGG (SEQ ID NO. 10), IM2: TTTCGTTT (SEQ ID NO. 11) and IM3: TCAAGCTTGA (SEQ ID NO. 12) as objects of analyses, of *Lactobacillus rhamnosus*, GM-020, on inhibition of lipogenesis were accessed. Moreover, the effects of five ODN fragments, each of which contained the core sequence, IM3, on inhibition of lipogenesis were tested in experiments. As shown in test results, GM-020 containing two specific oligodeoxynucleotide fragments proved effective in inhibiting lipogenesis significantly. In the present disclosure, the composition with probiotics or nucleotides as an effective ingredient has the advantageous characteristic of low side effects and can be taken as a novel and safe preventive measure for obesity attributed to fat-rich diets.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention.

FIG. 1B illustrates functional analyses of the whole genome of GM-020.

FIG. 1C illustrates sequencing analyses of GM-020.

DETAILED DESCRIPTION OF THE PREFERRED EMBODIMENTS

Figure 1A:
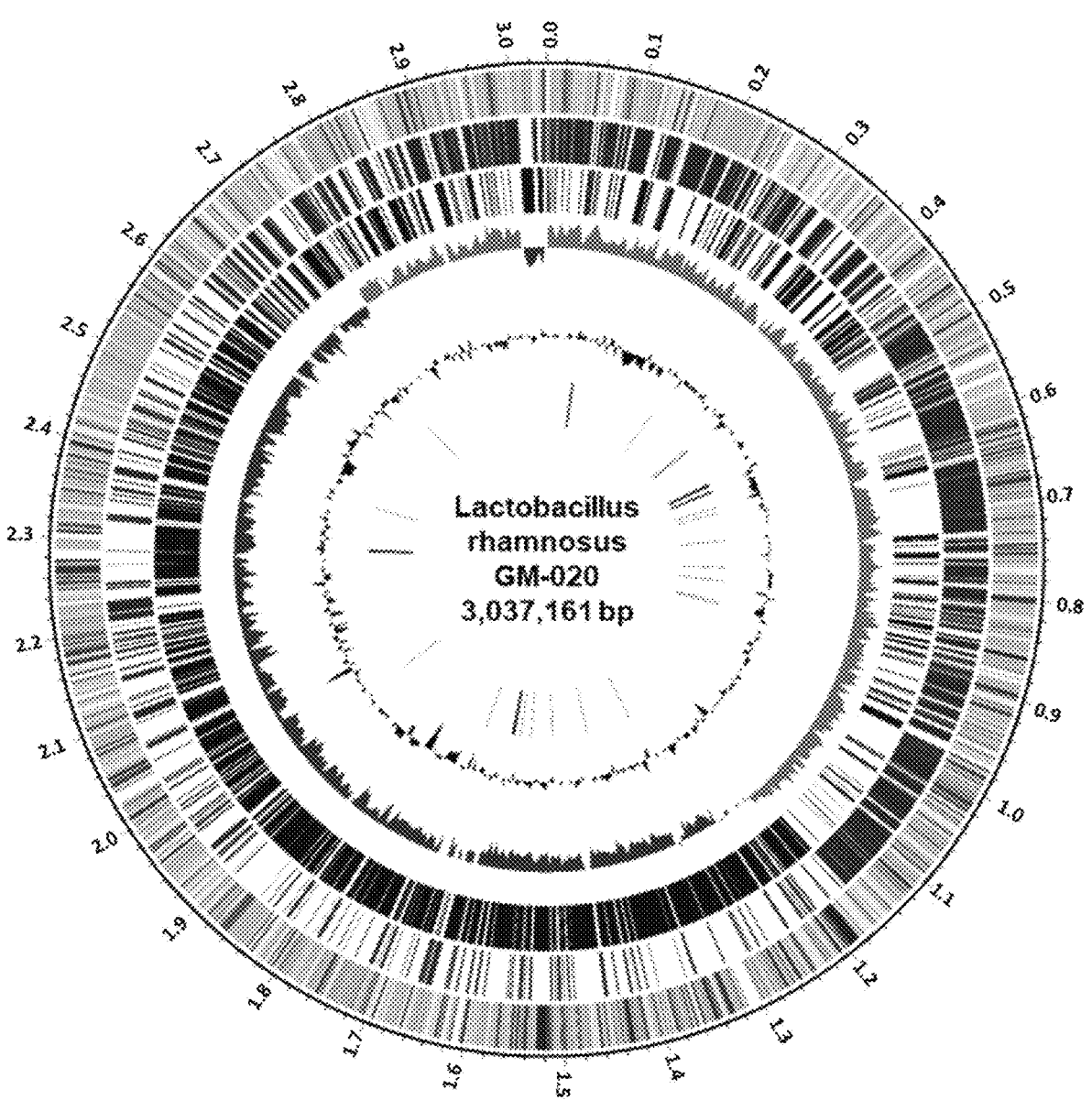
FIG. 1A illustrates circular genome data of the whole genome of GM-020.
Figure 1D:
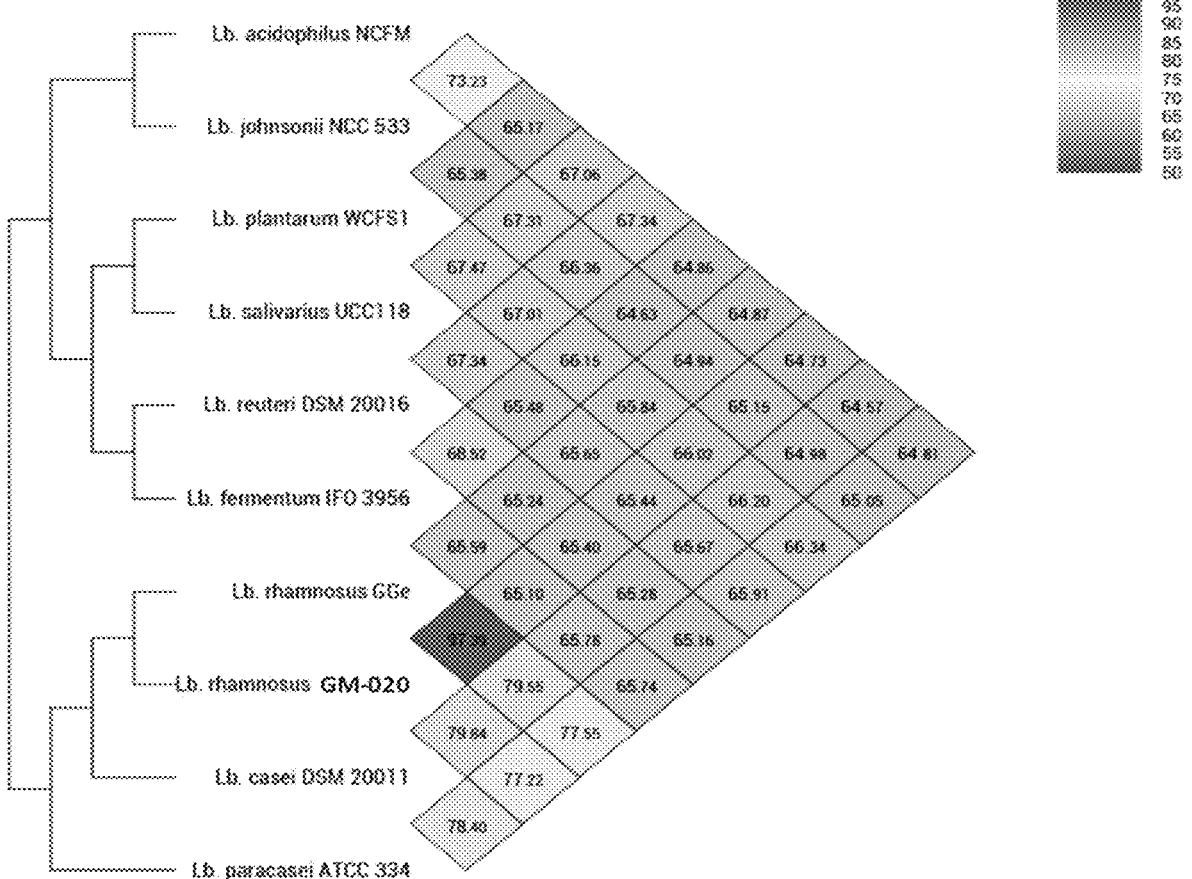
FIG. 1D illustrates speciational evolution of GM-020.
Figure 1E:
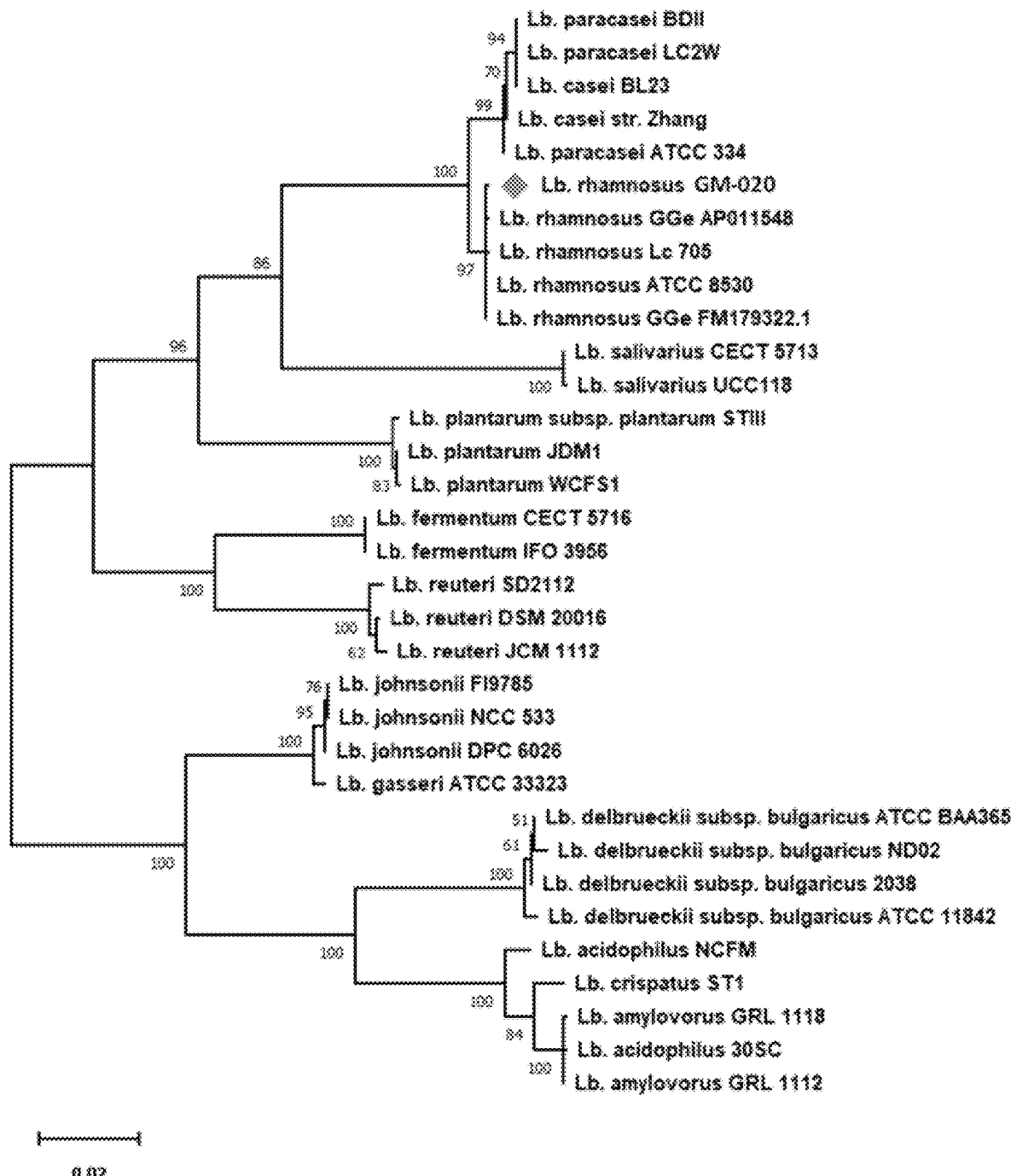
FIG. 1E illustrates speciational evolution of GM-020.

The technical and scientific terminologies in the patent specification are well known to persons with common knowledge in the art unless otherwise specified.

A singular noun joined by "a/an," "one," or "the" in the patent specification or claims may refer to more than one object unless otherwise specified.

Words like "or" or "and" refer to "and/or" unless otherwise specified. Moreover, words like "comprise" or "contain" are open-ended terms. The descriptions in a previous section refer to general involvement but are not interpreted as restrictions to the subject of the present invention.

The effective ingredients or the composition in the present disclosure, as well as at least a pharmaceutically acceptable vehicle, can be chosen by a person with common and well-known knowledge in the art for preparation of a formulation applicable to the composition. The formulation includes, without limitation, a solution, an emulsion, a suspension liquid, powders, a pastille, an oral ingot, a tablet, a chewing gum, a capsule, and another similar formulation applicable to the present invention.

The terminology of "pharmaceutically acceptable" means a substance or a composition and other components of a pharmaceutical concoction thereof being compatible with each other but not aggravating a patient's symptoms.

The terminology of "pharmaceutically acceptable vehicle" comprises one or more types of ingredients selected from: a solvent, an emulsifier, a suspension agent, a decomposing agent, a binding agent, an excipient, a stabilizing agent, a chelating agent, a diluent, a gelling agent, a preservative, a lubricating agent, a surfactant, and another similar vehicle applicable to the present invention.

One or more co-solvents, buffer agents, coloring agents, and flavoring agents common in the pharmaceutical industry can be discretionarily added in the composition as required.

The terminology of "pharmaceutical composition" means a solid or liquid composition with a form, concentration, and purity applicable to medicine administration for a patient from whom an expected physiological change is induced after administration. The pharmaceutical composition is sterile and/or non-pyrogenic.

The materials used in the patent specification are substances commercially available unless otherwise specified. *Lactobacillus rhamnosus* (also known as *Lacticaseibacillus rhamnosus*) GM-020, in an embodiment hereinafter, was deposited on Dec. 18, 2003 and has the designation number of CCTCC M203098 at the China Center for Type Culture Collection (CCTCC).

Embodiment 1, Whole Genome Sequencing of GM-020

Culturing and Sequencing of Probiotics 0.1 ml lactobacilli in 1 ml lactobacilli cultured overnight was instilled into 10 ml MRS broths for activation of second-generation strains and observation of the growth curve. After $OD_{600}$ of 0.8 was detected, 3 ml Lactobacillus broths were flushed twice with filtered sterile water (13,000 rpm; 1 min) and Lactobacilli remained were prepared for genomic DNA extraction. DNAs were extracted with QIAGEN DNeasy® Blood & Tissue Kit (QIAGEN; Cat. No. 69504). The quality of genomic DNAs was checked through the Qubit fluorometer, the nanophotometer, and agarose gels. The whole-genome DNA sequencing was done by Health GeneTech Corp. DNAs to be tested were sequenced with Illumina Hiseq 2000 (for next generation sequencing) and Nanopore GridION (for third generation sequencing), respectively.

Pretreatment of Sequence Assembly:

Low-quality noises inside sequencing data were filtered with FASTX-Toolkit and MinIONQC (Quality Value=20, that is, error rate per base=$1/100$) before sequence assembly, respectively.

Sequence Assembly and Correction of Sequencing Data:

The nucleotide sequences of the filtered high-quality second-generation sequencing short fragments and the third-generation sequencing data were assembled to be the longer continuous sequences with a published tool, MaSuRCA v3.3.1, based on the hybrid assembly method. The bridging sequences constructed were aligned based on the sequences of third-generation sequencing data for verification of the precedence relationship between contigs. Moreover, the variation test and the genome assembly improvement were completed by Pilon. With the Nanopore long-read sequence taken as a reference sequence, each discrepancy or gap of a single base in one reading was checked and corrected after short-read sequence alignment for reducing false positive.

Speciational Evolution Analysis, Sequencing Genome Annotation and Functional Pathway Analysis:

The sequence of a subtype strain collected after the sequence assembly and the sequence to be tested were checked during the multiple sequence alignment as a critical reference for completing the molecular evolution analysis, the evolutionary analysis, and traceability and facilitating rapid and accurate strain identification on the next-generation sequencing platform. The genome annotation was completed with several tools: Prokka for gene prediction of the whole genome of a procaryotic organism including protein coding and non-coding regions; Plasflow for plasmid identification; PHASTER for filtration of a phagore region inside a genome; Bagel4 & CARD for predictions of both genes correlated with generation of bacteriocin and probable drug resistance regions; eggNOG as one tool facilitating functional classifications on a region of functional proteins probably translated from a protein coding region and combined with the Cluster of Orthologous Genes (COG) of the protein database for annotations and classifications.

According to data analyses of the whole genome, genetic information and the phylogenetic tree, GM-020 is recognized as *Lactobacillus rhamnosus* and characteristic of the genome size of 3,037,161 bp. The whole genome, the functional analyses and the speciational evolution correlated with GM-020 are shown in FIG. 1A, FIG. 1B, FIG. 1C, FIG. 1D and FIG. 1E.

The frequency of IM1 (TTAGGG) (SEQ ID NO. 10), IM2 (TTTCGTTT) (SEQ ID NO. 11), and IM3 (TCAAGCTTGA) (SEQ ID NO. 12) sequences appearing in the whole genome were further analyzed in GM-020 and three other *Lactobacillus rhamnosus* strains, 4B15, DSM14870 and BPL5, as disclosed in published literature.

As summarized in Table 1, the frequency of IM1, IM2 and IM3 sequences in the whole genome was higher in GM-020 than in the other three *Lactobacillus rhamnosus* strains such as 4B15, DSM14870 and BPL5. It suggested that IM1, IM2, and IM3 sequences probably contribute to the specific functions of GM-020.

6

TABLE 2-continued

The five ODN sequences of GM-020 containing IM3 core sequence

| Code name | Core sequence | SequenceID | ODN sequences of GM-020 |
|---|---|---|---|
| IM3-4 | | SEQ ID NO. 4 | TCAGGCTCAAGCTTGAGTTC |
| IM3-5 | | SEQ ID NO. 5 | TAGGACTCAAGCTTGATCTC |

Embodiment 2, Syntheses of CpG-ODN and Pretreatment

Five ODN fragments, IM3-1, IM3-2, IM3-3, IM3-4 and IM3-5, chemically synthesized by Genomics BioSci & Tech Co., Ltd., were based on the location of TCAAGCTTGA (SEQ ID NO. 12), five nucleotide bases forward of 5' TCAAGCTTGA, and four nucleotide bases backward of TCAAGCTTGA3' in the GM-020 genome. After being rapidly centrifuged, the powdered form of synthesized DNA was diluted to 200 μM with sodium chloride. After 10 minutes, the solutions were continuously diluted and prepared to be stock solutions with concentrations of 100, 50, 25 and 12.5 μM, respectively.

Embodiment 3, Cultivation of Adipocytes

Preadipocyte 3T3-L1 was seeded in DMEM medium with 10% FBS for two days and occupied to be 70% confluent.

TABLE 1 the frequency of IM1, IM2 and IM3 sequences in the different strain of *Lactobacillus rhamnosus*

| Code | Sequence | Genome size (bp) | | GM-020 3,037,161 | 4B15 3,047,840 | DSM 148709 3,013,150 | BPL5 3,024,030 |
|---|---|---|---|---|---|---|---|
| IM1 | TTAGGG | Frequency | | 363 | 229 | 233 | 230 |
| | | No. copies per $10^6$ bases | | 11.96 | 7.51 | 7.73 | 7.60 |
| IM2 | TTTCGTTT | Frequency | | 98 | 60 | 66 | 65 |
| | | No. copies per $10^6$ bases | | 3.23 | 1.97 | 2.19 | 2.14 |
| IM3 | TCAAGCTTGA | Frequency | | 5 | 3 | 3 | 3 |
| | | No. copies per $10^6$ bases | | 0.16 | 0.10 | 0.10 | 0.10 |

Furthermore, the function of ODN with IM3 core sequence was tested with adipocytes. The five ODN sequences were characteristic of IM3 core sequence (TCAAGCTTGA) (SEQ ID NO. 12), and distinct sequences forward of 5' TCAAGCTTGA and backward of TCAAGCTTGA 3', named for IM3-1, IM3-2, IM3-3, IM3-4 and IM3-5, in Table 2.

TABLE 2

The five ODN sequences of GM-020 containing IM3 core sequence

| Code name | Core sequence | SequenceID | ODN sequences of GM-020 |
|---|---|---|---|
| IM3 | TCAAGCTTGA | | |
| IM3-1 | | SEQ ID NO. 1 | CCATTTTCAAGCTTGACTTT |
| IM3-2 | | SEQ ID NO. 2 | GACATTTCAAGCTTGAACAA |
| IM3-3 | | SEQ ID NO. 3 | TTGGTGTCAAGCTTGACATC |

Then, cell culture medium was replaced by induction medium (10% FBS DMEM+1 μM Dexamethasone, 0.5 mM 3-isobutyl-1-methyl-xathine (IBMX) and 10 μg/mL insulin) and further by growth medium (10% FBS DMEM+10 μg/mL insulin) two days later. The cells were stimulated with IM3-1, -2, -3, -4 and -5. The growth medium (10% FBS DMEM+10 μg/mL insulin) containing IM3-1, -2, -3, -4 and -5 were replaced every three days until the end of experiment.

Embodiment 4, Lipogenesis Test

The adipocytes 3T3-L1 differentiated were flushed twice with PBS. The adipocytes were immobilized with 4% paraformaldehyde (PFA) at room temperate for 0.5 to 1 hour and flushed twice with pure water. Then, 60% isopropanol was added to the adipocytes for five minutes and then absorbed. The adipocytes were stained with Oil Red O for 10 to 20 minutes and were flushed twice with pure water until no stain color observed. The adipocytes were dipped with 60% isopropanol for five minutes. Lipid droplets inside adipocytes were dissolved out by 250 μL of 100% isopropanol. Finally, 200 μL of lipid droplets were carried on a 96-well plate for measurement of the optical density (OD) at the wave length 492 nm.

Figure 2A:
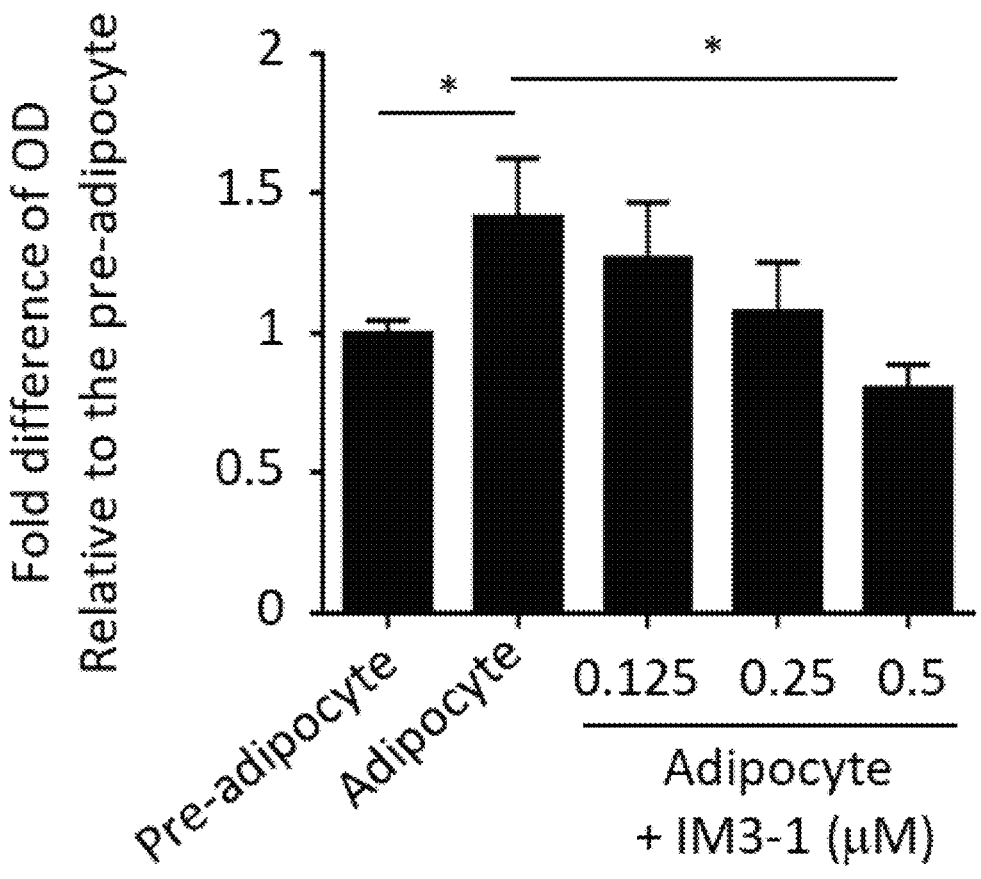
FIG. 2A illustrates the effect of IM3-1 on inhibiting lipid droplets generated.
Figure 2B:
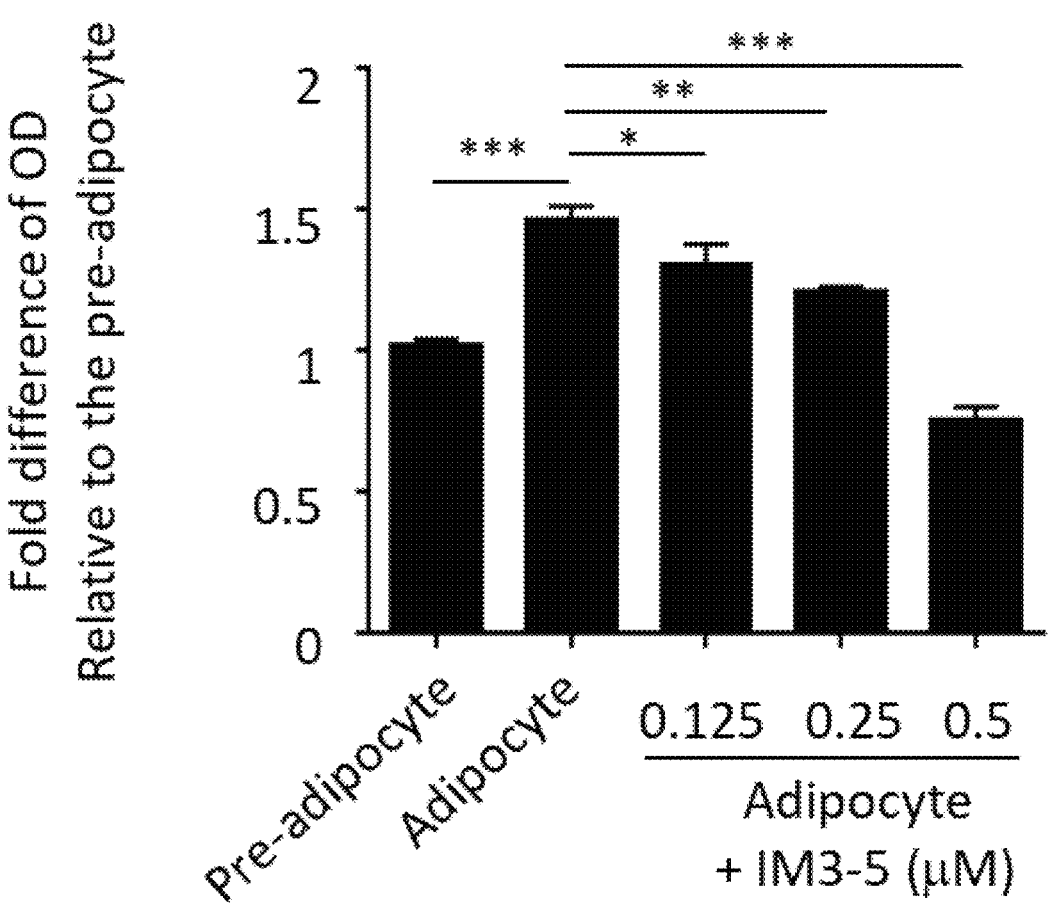
FIG. 2B illustrates the effect of IM3-5 on inhibiting lipid droplets generated.
Figure 3:
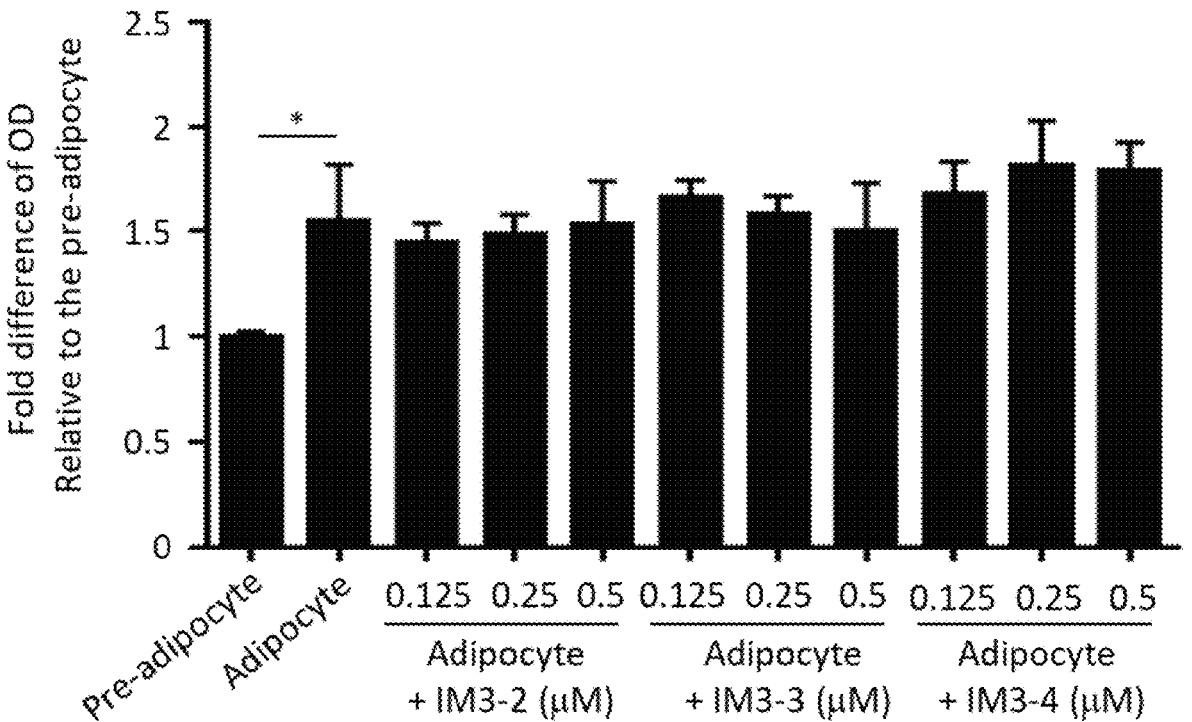
FIG. 3 illustrates no effect of IM3-2, IM3-3 or IM3-4 on inhibiting lipid droplets generated.

The differentiated adipocytes 3T3-L1 were stimulated with chemically synthesized IM3-1, -2, -3, -4, and -5, respectively. The intracellular lipid droplets were stained with Oil red O dyes and quantified based on the OD value. As shown in FIG. 2A and FIG. 2B, generation of lipid droplets in adipocytes were inhibited effectively when cells were stimulated with IM3-1 and IM3-5. In FIG. 3, IM3-2, IM3-3 and IM3-4 showed no effect on the inhibition of lipogenesis.

Embodiment 5, Expression of the FAS Gene (Lipogenesis-Related Gene)

RNA from adipocytes 3T3-L1 was extracted by TRIZol and to be a template transcribed to cDNA by Q-PCR mechine. Each reaction reagent contained 5 μL 2× Rotor-Gene SYBR Green PCR Master Mix (QIAGEN) in which 2 μL cDNA and 2 μL of 10 μM Forward (F)+Reverse (R) primers were added in turn. Primer sequences of FAS gene were (1) forward: GGAGGTGGTGATAGCCGGTAT (SEQ ID NO:6); (2) reversed: TGGGTAATCCATAGAGCCCAG (SEQ ID NO:7). Primer sequences of GAPDH gene were (1) forward: TGCACCACCAACTGCTTAGC (SEQ ID NO:8); (2) reversed: GGCATGGACTGTGGTCATGAG (SEQ ID NO:9). The reaction solution was placed inside the Q-PCR machine (model: QIAGEN Rotor-Gene Q 2Plex) for Real-time PCR (Real-time Pmerase Chain Reaction). After the house-keeping gene, GAPDH, and the amount of the relative expression for the control group, $(2^{-\Delta\Delta}Ct)$, were deducted from CT derived at Q-PCR in turn, the amount of gene expression was determined.

TABLE 3

The sequences of forward and reversed primer for FAS and GAPDH gene

| Primer name | Sequence ID No. | Nucleotide sequence |
|---|---|---|
| Forward primer of FAS gene | SEQ ID NO: 6 | GGAGGTGGTGATAGCCGGTAT |
| Reverse primer of FAS gene | SEQ ID NO: 7 | TGGGTAATCCATAGAGCCCAG |
| Forward primer of GAPDH gene | SEQ ID NO: 8 | TGCACCACCAACTGCTTAGC |
| Reverse primer of GAPDH gene | SEQ ID NO: 9 | GGCATGGACTGTGGTCATGAG |

Figure 4:
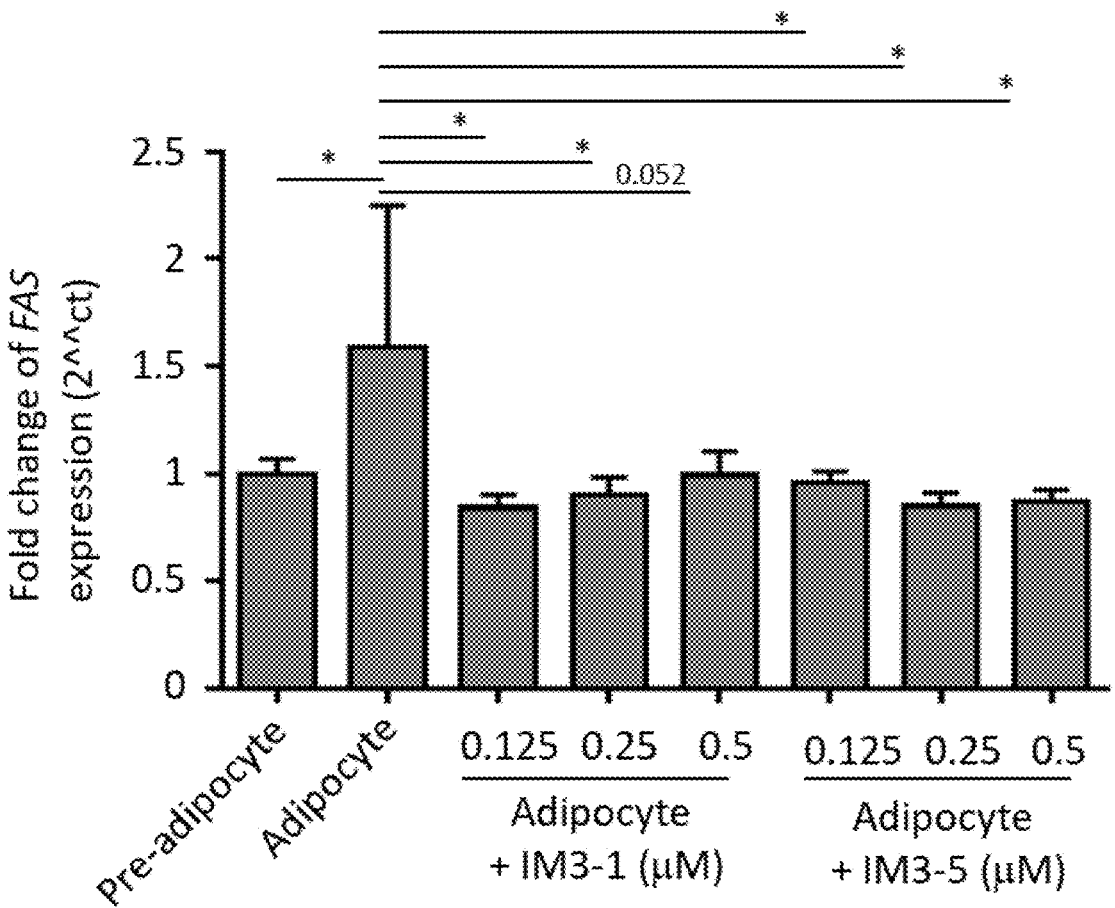
FIG. 4 illustrates the effect of IM3-1 or IM3-5 on inhibiting gene expression of FAS.

Lipogenesis-related gene, such as FAS (fatty acid synthase), was over-expressed in the cells which accumulated lipids excessively. Therefore, FAS gene expression was further checked after adipocytes were simulated with IM3-1 or IM3-5. By the analysis of RT-PCR, the activation of FAS gene expressing was inhibited after adipocytes were simulated with IM3-1 or IM3-5 (FIG. 4). It can be seen from the present disclosure that two ODN sequences from GM-020 genome, IM3-1 (CCATTTTCAAGCTTGACTTT) (SEQ ID NO. 1) and IM3-5 (TAGGACTCAAGCTTGATCTC) (SEQ ID NO. 5), significantly inhibited lipid generation through down-regulating the lipogenesis-related gene expression, such as FAS.

The core sequence, TCAAGCTTGA (SEQ ID NO: 12), was unexceptionally contained in the five ODN fragments However, the sequence connecting with 5' and 3' ends of TCAAGCTTGA was distinct among the fragments. The results showed that the five ODN fragments had varying effect on the inhibition of lipogenesis. Only IM3-1 or IM3-5 exhibited a significant effect on lipogenesis inhibition, while IM3-2, IM3-3 or IM3-4 did not demonstrate the significant effect on lipogenesis inhibiting. In the present invention, through experimental measures such as the lipogenesis test and lipogenesis-related FAS gene expression, ODN fragments with health benefits provide a novel and safe prevention and improvement strategy for improving obesity caused by high-fat diet.

As disclosed in preferred embodiments of the patent specification, the embodiments are only examples well known to persons skilled in the art and having common knowledge. Any change or modification of the technical features in the patent specification made by persons skilled in the art and having common knowledge should not be taken as differences from the features in the present disclosure. The present invention could be fulfilled based on embodiments in the patent specification and even other changes in embodiments. As defined in claims of the patent specification, the scope of the present invention should cover the method as well as architecture mentioned above and any equivalent modification.

As presented in many effects hereinbefore, an application based on nucleotides of *Lactobacillus rhamnosus* to prepare a composition for anti-lipogenesis in the patent specification meets novelty and non-obviousness for patentability.

The above detailed descriptions are feasible embodiments of an application based on nucleotides of *Lactobacillus rhamnosus* to prepare a composition for anti-lipogenesis that should not restrict the scope of the present application. Any equivalent implementation or modification without departing from the spirit and scope of the present application should be incorporated in claims hereinafter.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

As presented in many effects hereinbefore, an application based on nucleotides of *Lactobacillus rhamnosus* to prepare a composition for anti-lipogenesis in the patent specification meets novelty and non-obviousness for patentability.

Biological Material Deposit

*Lactobacillus rhamnosus* (also known as *Lacticaseibacillus rhamnosus*) GM-020 was deposited on Dec. 18, 2003 and has designation number CCTCC M203098 at the China Center for Type Culture Collection (CCTCC).

What is claimed is:

1. A method of preparing a pharmaceutical composition comprising adding SEQ ID No. and/or and SEQ ID No. 5 to a composition comprising a pharmaceutical excipient and/or a pharmaceutical vehicle.

2. A method of inhibiting lipid droplet formation in adipocytes in vitro comprising the administration of a composition comprising SEQ ID No. 1 and/or SEQ ID No. 5.

3. A method of inhibiting the expression of fatty acid synthase (FAS) in adipocytes in vitro comprising the administration of a composition comprising SEQ ID No. 1 and/or SEQ ID No. 5.

*     *     *     *     *